(12) United States Patent
Fisher et al.

(10) Patent No.: US 7,914,148 B2
(45) Date of Patent: Mar. 29, 2011

(54) OPHTHALMIC LENS SIMULATION SYSTEM AND METHOD

(75) Inventors: Scott Fisher, Flagstaff Hill (AU); Warwick Freeland, Somerton Park (AU)

(73) Assignee: Carl Zeiss Vision Australia Holdings Limited, Lonsdale (AU)

( * ) Notice: Subject to any disclaimer, the term of this patent is extended or adjusted under 35 U.S.C. 154(b) by 165 days.

(21) Appl. No.: 12/084,976

(22) PCT Filed: Nov. 15, 2006

(86) PCT No.: PCT/AU2006/001695
§ 371 (c)(1), (2), (4) Date: Jul. 1, 2008

(87) PCT Pub. No.: WO2007/056795
PCT Pub. Date: May 24, 2007

(65) Prior Publication Data
US 2008/0316427 A1    Dec. 25, 2008

(30) Foreign Application Priority Data
Nov. 15, 2005    (AU) ................................. 2005906335

(51) Int. Cl.
*A61B 3/02* (2006.01)
*A61B 3/00* (2006.01)
*A61B 3/10* (2006.01)

(52) U.S. Cl. .................... 351/233; 351/200; 351/205

(58) Field of Classification Search ............... 351/233, 351/200, 203, 205, 211, 246
See application file for complete search history.

(56) References Cited

U.S. PATENT DOCUMENTS

| 6,160,666 A | 12/2000 | Rallison | |
|---|---|---|---|
| 6,947,219 B1 * | 9/2005 | Ou | 359/630 |
| 2001/0026351 A1 * | 10/2001 | Gao et al. | 351/227 |

FOREIGN PATENT DOCUMENTS

| EP | 1 468 649 A1 | 10/2004 |
|---|---|---|
| EP | 1 515 179 A1 | 3/2005 |
| JP | 11-120213 A | 4/1999 |
| WO | WO 01/88654 A2 | 11/2001 |
| WO | WO 03/087889 A2 | 10/2003 |

OTHER PUBLICATIONS

International Search Report (PCT/ISA/210).
International Search Report dated Oct. 8, 2009 for European Application No. 06804515.2-2224/1949174.
English Abstract and Machine Translation for Japanese Patent Publication No. 11-120213, Published Apr. 30, 1999.

* cited by examiner

*Primary Examiner* — Ricky L Mack
*Assistant Examiner* — Dawayne A Pinkney
(74) *Attorney, Agent, or Firm* — Buchanan Ingersoll & Rooney PC

(57) ABSTRACT

A method of simulating an optical effect, and/or characteristic of a selected ophthalmic lens design for a wearer is disclosed. In an embodiment, the method includes retrieving simulation data for the selected ophthalmic lens design and processing the simulation data to generate output image data for an output image simulating the optical effect and/or characteristic of the selected ophthalmic lens design. The output image is displayed, using a head-mounted display worn by the wearer, for viewing by the wearer.

A system for simulating an optical effect, and/or characteristic of a selected ophthalmic lens design for a wearer is also disclosed.

13 Claims, 10 Drawing Sheets

OPHTHALMIC LENS SIMULATION SYSTEM AND METHOD

This application claims priority from Australian Provisional Patent Application No. 2005906335 filed on 15 Nov. 2005, the contents of which are to be taken as incorporated herein by this reference.

FIELD OF THE INVENTION

The present invention relates to the dispensing of ophthalmic lenses. In a typical application, the present invention may be used by an optometrist to assist in the dispensing of single vision, bifocal, or progressive addition lenses for a person ('the wearer').

BACKGROUND OF THE INVENTION

Traditionally, dispensing of ophthalmic lenses for a wearer typically involves fitting the wearer with ophthalmic lenses having different optical characteristics, and by way of a trial-and-error process, selecting a particular lens having optical characteristics that are considered to provide a desired optical performance.

Unfortunately, after dispensing the selected lenses, the person may be dissatisfied with the selected lenses, perhaps because the process of selecting the lens did not provide, for the wearer, a suitable visual experience of the lens performance.

It is an aim of the present invention to provide a system and method that provides a person with a visual experience that assists the person in making a design selection, or at least in gaining an improved understanding of the design factors having a bearing on their decision.

SUMMARY OF THE INVENTION

The present invention provides a method of simulating an optical effect and/or characteristic of a selected ophthalmic lens design for a wearer, the method including: retrieving simulation information for the selected ophthalmic lens design; processing the simulation information to generate output image data for an output image simulating the optical effect and/or characteristic of the selected ophthalmic lens design; and displaying, using a head-mounted lens simulator unit worn by the wearer, the output image for viewing by the wearer.

The use of a head-mounted lens simulator unit is expected to provide a useful simulation experience for the wearer since the simulation will replicate the selected ophthalmic lens design in an "as worn" position.

The ophthalmic lens design may be selected from a piano ophthalmic lens design, a single vision ophthalmic lens design or a multi-focal ophthalmic lens design (such as a bi-focal or a progressive addition lens). The selected ophthalmic lens design will typically be modelled using the simulation information. The simulation information will be described in more detail later.

The simulated optical effect may vary according to the type of ophthalmic lens design being simulated, and may include one or more of effects due to simulated optical parameters associated with the simulated ophthalmic lens design such as sphere (Rx), cylinder (Cyl), axis, addition power, astigmatism, prism, and base.

It will be understood that different ophthalmic lens designs have different optical parameters and thus will have a different optical effect on the wearer. In this respect, in referring to "optical effect", we mean any optical effect which would be visible to, or experienced by, the wearer as a result of the optical properties of an ophthalmic lens corresponding with the selected ophthalmic lens design. Thus, in addition to an optical effect arising from the simulated optical parameters listed above, other optical effects may also be simulated, such as motion induced blur, tint, lens surface coatings (such as a UV coating), filters and the like.

The characteristic of the selected ophthalmic lens will typically include one or more characteristics of lens geometry that would not normally be classified as optical effects per se, but that nevertheless have a bearing on the overall optical properties of the selected ophthalmic lens design, or at least on an optical interaction between the selected ophthalmic lens design and the wearer. For example, the characteristic may include the size of the lens or the shape of the perimeter of the lens. Additional characteristics may be simulated for different lens types. For example, for a bi-focal lens the characteristic may also include segment boundaries. In addition, for a progressive addition lens the characteristic may also include one or more of zone boundaries, zone size balance and inset.

The simulated optical effect and/or characteristic may simulate the approximate visual experience that would be experienced by the wearer when viewing though an ophthalmic lens corresponding with the selected ophthalmic lens design. To achieve that, the simulation information will typically include data, in the form of simulation data, that parameterises optical properties of the selected ophthalmic lens that are associated with the surface shape of the simulated lens design. However, this need not always be the case. For example, in another embodiment the simulation data parameterises optical properties such as one or more of different frames, tints, or lens treatments.

The simulation information for a selected ophthalmic lens design may be retrieved from a database containing simulation information for plural ophthalmic lens designs. In such an embodiment, a user may operate a user interface so as to select, from the database, a particular ophthalmic lens design for the simulation.

The output image data may have any format suitable for display by the head-mounted display. Typically, the output image data will be in the form of a output image file containing data that can be decoded as a still image (such as a photographic image). For such an embodiment, the output image file may have any suitable digital format, such as a joint photographic experts group (jpeg) format, a graphics interchange format (gif), portable network graphics format (png), bitmap, tagged image file format (tiff). For an output image file containing data that can be decoded as a video image (such as a computer generated video image), the output image file may have a suitable digital video format, such as an audio video interleave format (avi), a moving picture expert group file (mpeg) format, a macromedia flash movie format, a windows media video format or a real media format.

In one embodiment, the output image data includes data that can be decoded for display on the head mounted display as an output image including lens features representing a characteristic of the lens and scene features representing a real or computer generated scene. For example, the output image may include lens features that are superimposed over an image obtained from another source, such as one or more cameras fitted to the lens-simulator unit. In one embodiment, the lens features represent lens boundaries that displayed as, for example, lines (such as contours) or shaded regions so as to identify the, or each, boundary. The lens features are then displayed as an output image that includes the lens features superimposed over a real or computer generated scene.

The lens boundaries may include, for example, segment boundaries (such as bi-focal segment boundaries), zone boundaries (such as, distance zone, near zone and corridor boundaries for a progressive addition lens), contours of equal astigmatism, contours of equal refracting power, or a perimeter (such as a perimeter for a particular frame size).

In one embodiment, in which the selected ophthalmic lens is a progressive addition lens, the lens features representing the different zones of the lens may be displayed as shaded regions having a different colour or pattern for each zone.

It is envisaged that an embodiment that provides output image data including lens features superimposed over scene features may assist a person in selecting an ophthalmic lens that meets their requirements, or at the very least, assist them in understanding the significance of those features in making their lens selection.

In an alternative embodiment, the simulation data also includes input image data that is processed to generate output image data for an output image simulating the optical effect and/or characteristic on the input image encoded as input image data. Thus, in such an embodiment, the simulation information may include an input image file containing input image data for an input image (such as an image based on a 3D model) and a lens model information, in the form of one or more lens model files for the selected ophthalmic lens design.

The lens model information will typically model geometric distortions and or optical errors from an ideal focus condition, and will typically include a blur matrix and/or a distortion matrix. During a simulation, the blur matrix and the distortion matrix may be mapped onto the input image. The blur and distortion matrices may be generated by ray-tracing through a model of the lens in a conventional manner.

The lens model information may thus include information modelling parameters of the front and/or back surfaces of the selected ophthalmic lens design. Other parameters such as refractive index, centre thickness and position of wear may also be modelled to match a particular application for the selected ophthalmic lens design.

In one embodiment of the present invention that simulates the visual distortions of the selected ophthalmic lens design, the simulation may entail mapping the distortion matrix onto the input image represented by the image data. In such an embodiment, image points in the input image are moved, by way of a mathematical manipulation, so as to match the location in the distortion matrix. Once the mathematical manipulations have been completed the output image data is output to the head mounted display unit for display.

In an embodiment that processes input image data, the input image data may have any suitable format. Typically, the input image data will be in the form of an input image file containing digital data that can be decoded for display as a still or video image. In one embodiment, the input image data includes data that can be decoded to display a computer generated scene, such as a computer generated animated scene, or a computer generated still scene. In such an embodiment, the output image data includes data that can be decoded to reproduce the computer generated scene modified in accordance with the optical effect and/or characteristic of the selected ophthalmic lens design.

In another embodiment, the input image data includes video or still image data captured, using one or more cameras fitted to the wearer's head for capturing a viewing activity conducted by the wearer prior to, or during, the simulation. In other words, in one embodiment, one or more cameras are arranged to capture the "view" of the wearer during the viewing activity. The viewing activity may include, for example, a near field viewing activity, such as reading, or a distance field viewing activity. In such an embodiment, the output image data may include data that can be decoded to display the captured video image, or the captured still image, modified in accordance with the simulated optical effect and/or characteristic of the selected ophthalmic lens design.

Thus, the present invention also provides a method of simulating an optical effect and/or characteristic of a selected ophthalmic lens design for a wearer, the method including: providing an input image capturing a viewing activity undertaken by the wearer; retrieving simulation information for the selected ophthalmic lens design; processing the input image and the simulation information to generate, for display to the wearer, an output image simulating the optical effect and/or characteristic of the selected ophthalmic lens design; and displaying, using a head-mounted display worn by the wearer, the output image for viewing by the wearer.

An embodiment of the present invention that provides an output image resulting from processing an input image capturing a viewing activity undertaken by the wearer provides the wearer with the capability to make comparisons between the different visual experiences provided using different ophthalmic lens designs, and to also gain an understanding of the optical effect and/or characteristic provided by ophthalmic lens design.

In an embodiment, generating the output image data includes processing feedback sensed during a wearer viewing activity. Processing the feedback may provide, for example, an output image file that simulates a motion induced optical effect.

In one embodiment, the output image incorporates a simulated optical effect and/or characteristic resulting from processing eye-tracking information. For example, the size and shape of the clear viewing areas of a PAL may be mapped to preferred eye movements of the wearer in order to select a progressive ophthalmic lens design, an optical effect and/or characteristic for which is then simulated for the wearer.

In another embodiment, the output image incorporates a simulated optical effect and/or characteristic resulting from processing an acuity measurement. For example, a wearer's visual acuity may be measured in terms of optical errors, and the effect of those errors displayed in an output image (and amplified if required) in order to educate the wearer about their condition and the possible solutions to it.

In yet another embodiment, processing the input image uses feedback derived from wave front-sensing. For example, an output image can be displayed that simulates various types of higher order aberration, spherical aberration, coma and trefoil for example. The effect of these errors on an input image can be displayed (and amplified if required) to educate the customer about their condition and the possible solutions to it.

In yet another embodiment, the output image incorporates a simulated optical effect and/or characteristic resulting from processing head movement information. For example, one embodiment of the present invention utilises head tracking sensors and software so as to obtain head movement information for the wearer either during a viewing activity conducted prior to the simulation, or during a viewing activity conducted during the simulation itself. In such an embodiment, the simulation information will include head movement information so that processing the simulation information and the input image generates a output image, typically in the form of a computer generated output image file, incorporating a motion induced optical effect, such as motion induced blur.

Any suitable head-mounted display may be used. One suitable head-mounted display includes a miniature liquid crystal display (LCD) fitted to a conventional pair of spectacle frames so that the display is located in a central vision region of an eye of the wearer.

In an embodiment, a single display is provided, in which case the present invention may simulate an optical effect and/or characteristics for monocular vision. In another embodiment, separate displays are provided for each eye of the patient, in which case the invention may simulate an optical effect for binocular vision. An embodiment that includes dual displays is expected to offer additional advantages over a single display embodiment since the use of dual displays may permit the invention to simulate a different ophthalmic lens design for each eye.

In an embodiment, the output image includes frame image features defining a field of view (FOV) boundary framing a field of view for the parts of the output image subject to a simulated optical effect or characteristic. In other words, the frame defines a boundary for the parts of the output image that related to the simulated ophthalmic lens. Typically, the field of view defined by the frame will be within a similar range to that provided by available conventional spectacle frames. As a result, in such an embodiment, and in addition to simulating an optical effect and/or characteristic of a selected ophthalmic lens design, the simulation will also provide the wearer with a visual experience that replicates, at least to some extent, the view as viewed through the frame. In such an embodiment, the vertical and horizontal angular size of the output image will typically exceed the corresponding angular sizes of the frame image features.

The present invention also provides a system for simulating the optical effect and/or characteristic of an ophthalmic lens design for a wearer, the system including: a simulation file containing simulation information for the selected ophthalmic lens design; a programmed computer including a simulation engine for processing the simulation information to generate output image data for an output image simulating the optical effect and/or characteristic of the selected ophthalmic lens design; and a lens simulator including a head-mountable display for displaying the output image to the wearer.

The present invention also provides a system for simulating an optical effect and/or characteristic of a selected ophthalmic lens design for a wearer, the system including processor and associated memory device for storing a series of instructions to cause the processor to: retrieve simulation information for the selected ophthalmic lens design; process the simulation information to generate output image data for an output image simulating the optical effect and/or characteristic of the selected ophthalmic lens design; and displaying, using a head-mounted lens simulator unit worn by the wearer, the output image for viewing by the wearer.

The present invention also provides computer software for use in a system for simulating an optical effect and/or characteristic of a selected ophthalmic lens design for a wearer, the system including a processor and associated memory device for storing the computer software including a series of instructions to cause the processor to: retrieve simulation information for the selected ophthalmic lens design; process the simulation information to generate output image data for an output image simulating the optical effect and/or characteristic of the selected ophthalmic lens design; and displaying, using a head-mounted lens simulator unit worn by the wearer, the output image for viewing by the wearer.

It is anticipated that system and method embodiments of the present invention will be useful for educational or marketing purposes. However, it is expected that the present invention will find primary use in displaying potential product candidates that a person could experience prior to purchasing, or in the case of an ophthalmic lens elements requiring laboratory manufacture, prior to manufacture.

BRIEF DESCRIPTION OF THE DRAWINGS

The present invention will now be described in relation to a preferred embodiment as illustrated in the accompanying drawings. However, it must be appreciated that the matter illustrated presents only one technique for embodying the invention. Other configurations and arrangements are envisaged as also being within the scope of the invention as generally described above.

In the drawings.

DETAILED DESCRIPTION OF EMBODIMENTS

Figure 1:
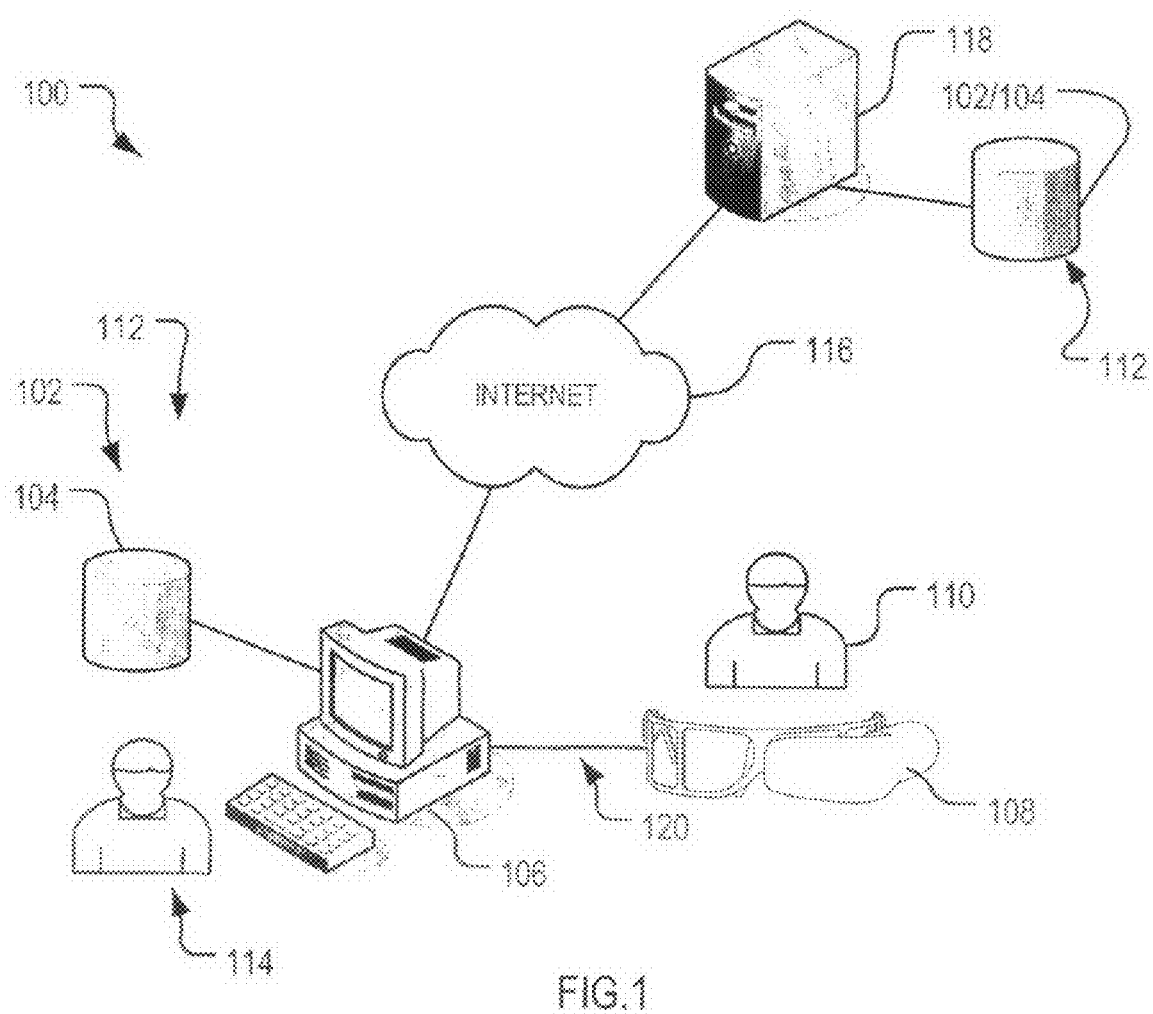
FIG. 1 is a simplified block diagram of a system in accordance with an embodiment of the present invention.

FIG. 1 shows a simplified block diagram of a system 100 according to an embodiment of the present invention. The system 100 includes a programmed memory 102 storing simulation information in the form of one or more simulation files 104, a programmed computer 106, and a lens simulator unit 108.

In the present case the one or more simulation files 104 include a lens model simulation file in the form of a distortion matrix or a blur matrix, and input image information in the form of an input image file containing image data. The distortion matrix or blur matrix may be generated by ray-tracing through a model of the lens in a conventional manner. Typically, a different lens model file will be provided for the left and right eyes of the wearer.

The input image file will have any suitable format that can be processed by the programmed computer 106 to provide output image data for an output image that is able to be displayed to a wearer 110 by way of a head-mounted display fitted to the lens simulator unit 108.

Typically, the input image file will contain input image data in the form of digital data that can be decoded for display as a still or video image. For example, the input image file may contain digital data for a computer generated video image or a computer generated still image.

Alternatively, the input image file may contain digital data for a video image or a still image recorded by one or more cameras fitted to the head-mounted display prior to conducting the simulation.

The simulation information for the selected ophthalmic lens design will typically be retrieved from a database 112 of simulation files containing simulation data for plural ophthalmic lens designs. In such an embodiment, a user 114 may operate the programmed computer 106 to select a particular ophthalmic lens design for the simulation. As shown, the database 112 may be local to the programmed computer 106, or it may a remote database 112 that is accessible by way of a suitable communications network (shown as the Internet 116 and server 118).

The lens simulator unit 108 and the programmed computer 106 are connected via interface 120. The interface 120 may include a wired interface. However, technological developments may permit the connections to be wireless, eliminating the need for a wired interface. Alternatively, the programmed computer 106 and the lens simulator unit 108 may be integrated as a single module.

The programmed computer 106 may include a wearable computer, a mobile computer (such as a laptop computer or a hand held computer), or a desktop computer. Suitable computer hardware 106 would be known to a skilled person.

Figure 2:
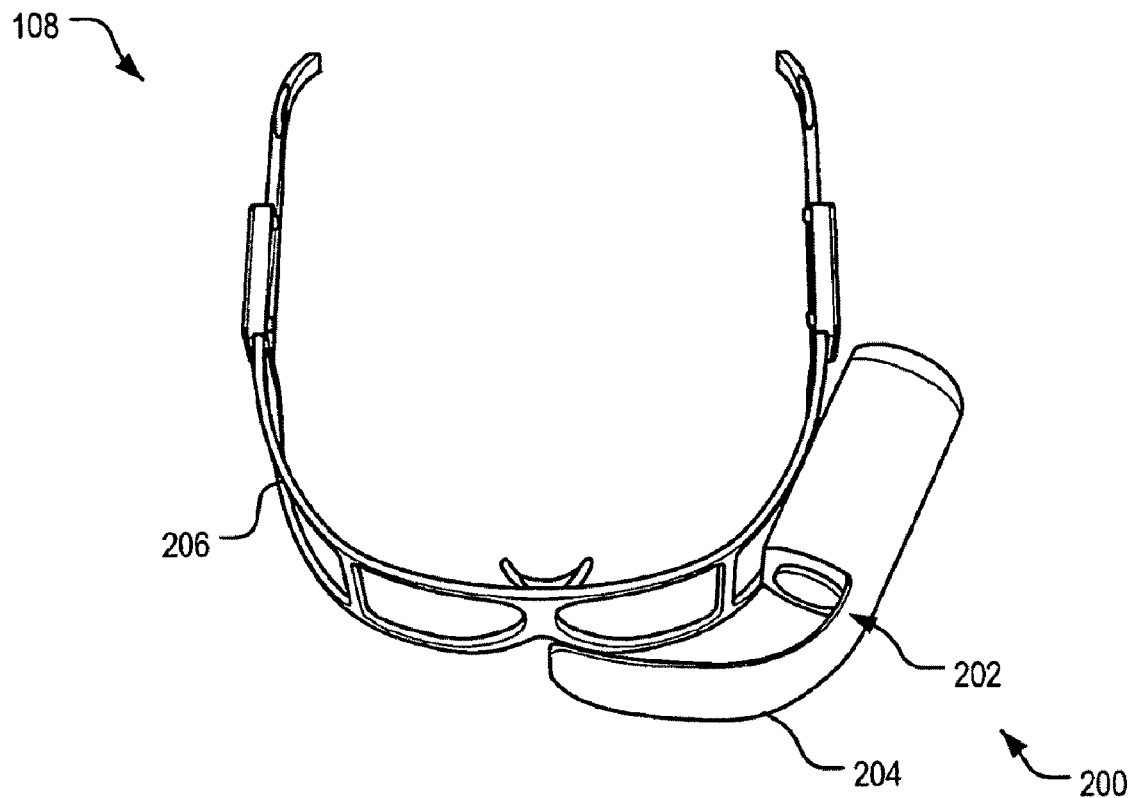
FIG. 2 is a top view of a first embodiment of a lens simulator unit suitable for use with the system of FIG. 1.
Figure 3:
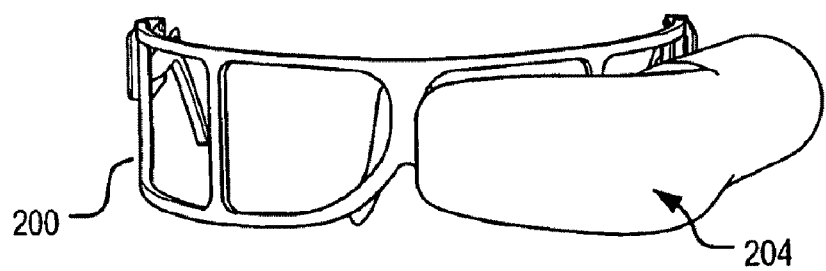
FIG. 3 is a front view of the lens simulator unit shown in FIG. 2.
Figure 4:
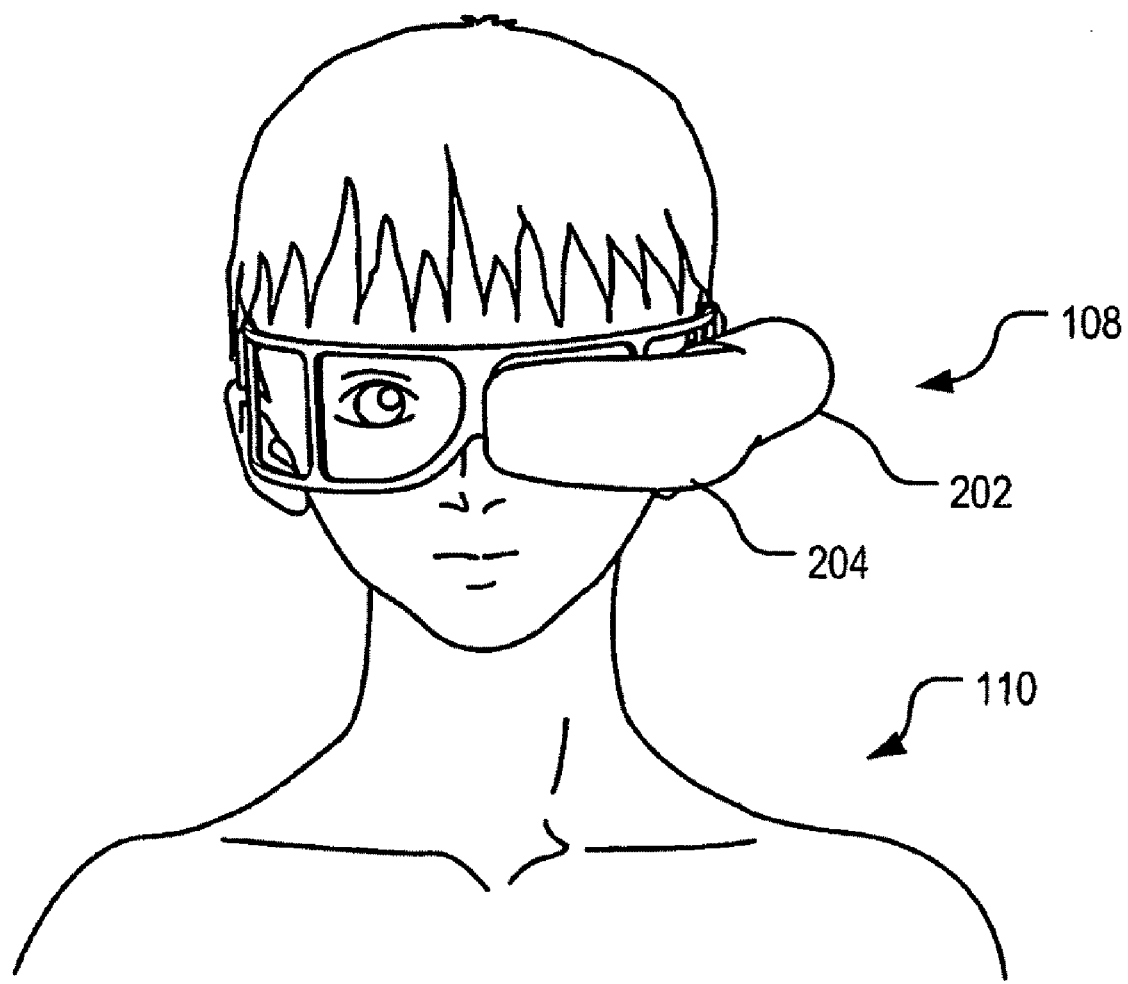
FIG. 4 is a front view of the lens simulator unit shown in FIG. 2 fitted to a wearer.

As is depicted in FIG. 2 to FIG. 4, the lens simulator unit 108 includes a head-mounted display (ref. FIG. 2) that is able to be fitted to the wearer 110 (ref. FIG. 4) in a manner similar to conventional spectacle frames to display an output image for viewing by the wearer 110. The output image will provide an approximate visual simulation of an optical effect, or characteristics, of a selected simulated ophthalmic lens design for the wearer 110 (ref. FIG. 1).

The simulated optical effect and/or characteristics will typically vary according to the type of ophthalmic lens being simulated by the system 100 (ref. FIG. 1). In this respect, a system 100 (ref. FIG. 1) in accordance with an embodiment of the present invention may simulate multiple types of ophthalmic lens designs, or it may simulate a single type. Thus, different embodiments of the present invention may be able to simulate an optical effect and/or characteristic of different ophthalmic lens types, including, for example, piano lenses, single vision lens, bi-focal lenses and progressive addition lenses (PAL).

For a single vision ophthalmic lens, the simulated optical effect may include an optical effect due to the sphere (Rx), cylinder (cyl), axis of the simulated ophthalmic lens design, or it include effect a motion induced blur optical effect. For a bifocal ophthalmic lens, the simulated optical effects may also include segment boundaries.

In relation to the simulation of a progressive addition lens (PAL), a different optical effect may be simulated for each of the different zones of the PAL. For example, different optical effects may be represented for one or more of the distance zone, the near zone, the corridor of low astigmatism connecting the distance zone to the near zone, and the peripheral zones. For each zone, the simulation may simulate astigmatism effects, refracting power effects, and motion induced blur effects. In terms of the simulating characteristics of a PAL, those characteristics may include, for example, zone size balance, inset, zone boundaries.

Irrespective of which type of ophthalmic lens is simulated, embodiments of the present invention will permit a wearer to experience a visual simulation that may assist with the selection of a suitable lens design for the wearer, in the sense that the wearer will "see" the optical effect and/or characteristics of the simulated ophthalmic lens in a typical viewing position. Such a visual simulation may assist the wearer in selecting an ophthalmic lens design that meets their visual needs. As a result, it is envisaged that embodiments of the present invention will find application in designing or dispensing ophthalmic lenses for a wearer.

The lens simulator unit 108 may include several components that are presently commercially available. For example, the lens simulator unit 108 may include a head-mounted display such as one available from Liteye Systems, Inc., Centennial, Colo., USA. The lens simulator unit 108 may include a monocular head mounted display or, alternatively, it may include a binocular head mounted display, depending on the type of simulation required.

Referring again to FIG. 2 there is shown a lens simulator unit 108 suitable for use with a first embodiment of the present invention. The lens simulator unit 108 includes a monocular head-mounted display 200 which itself includes a display projector 202 and a display surface 204, both of which are shown attached to a frame 206. It will of course be appreciated that other head-mounted display configurations may be used.

The display projector 202 includes a miniature liquid crystal display LCD) and an associated lens system for focusing the output image onto the display surface 204 so that the image is viewable by the wearer. Although the illustrated embodiment uses a LCD type projector, it is to be understood that other types of displays may be used, including for example, cathode ray tube (CRT), Liquid Crystal on Silicon (LCoS), or Organic Light Emitting Diode (OLED) displays.

The display surface 204 is supported by the frame 200 and is positioned to provide a surface for displaying the output of the display projector 202 for viewing by the wearer. The type, configuration and properties of the display surface 204 may vary for different lens simulator units 102. For example, the display surface may include a reflective, or partially reflective surface arrange to reflect the output image from the display projector 202 into the wearers eye. Alternatively, the display surface 204 may include a lens, or lens system, located between the display projector 202 and the wearer's eye, or a combination of a mirrored surface and a lens. Suitable display surfaces, including suitable lens and/or mirror arrangements, would be within the knowledge of a skilled person.

As shown in FIG. 4, the display projector 202 and the display surface 204 are arranged to display the output image in a central vision region of a single eye of the wearer 110 so as to be suitable for a monocular simulation.

Figure 5:
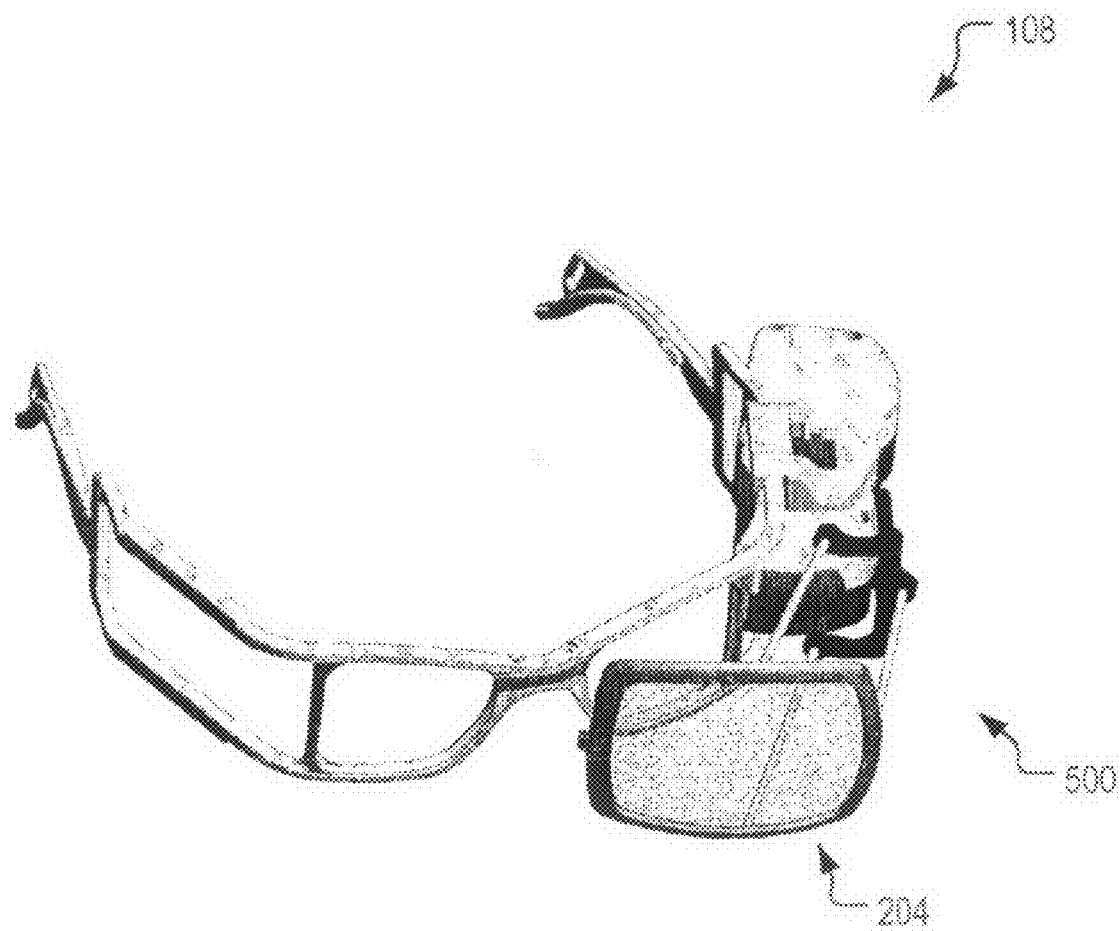
FIG. 5 is a perspective view of a second embodiment of a lens simulator unit suitable for use with the system shown in FIG. 1.

In the lens simulator unit 108 depicted in FIG. 2, the display surface 204 is opaque. However, in other embodiments a transparent or translucent display surface 204 may be provided. For example, FIG. 5 depicts a head-mounted display 500 of a lens simulator unit 108 suitable for use with a second embodiment of the present invention. The head-mounted display 500 includes a reflective surface 204 that is transmissive, or at least partially transmissive, to visible light (in other words, the surface is transparent or translucent). A lens simulator unit 108 that includes a transparent or translucent reflective surface 204 will permit a wearer to see through the display surface 204 and thus simultaneously view the output image superimposed on a real image scene in the field of view of the wearer. In such an embodiment, the head mounted display 500 is a "head-up" see through type display. Such an embodiment may be used, for example, to display simulated lens features, such as segment boundaries (in the case of a bi-focal ophthalmic lens), or zone boundaries (in the case of a progressive addition ophthalmic lens), superimposed over a real image.

Figure 6:
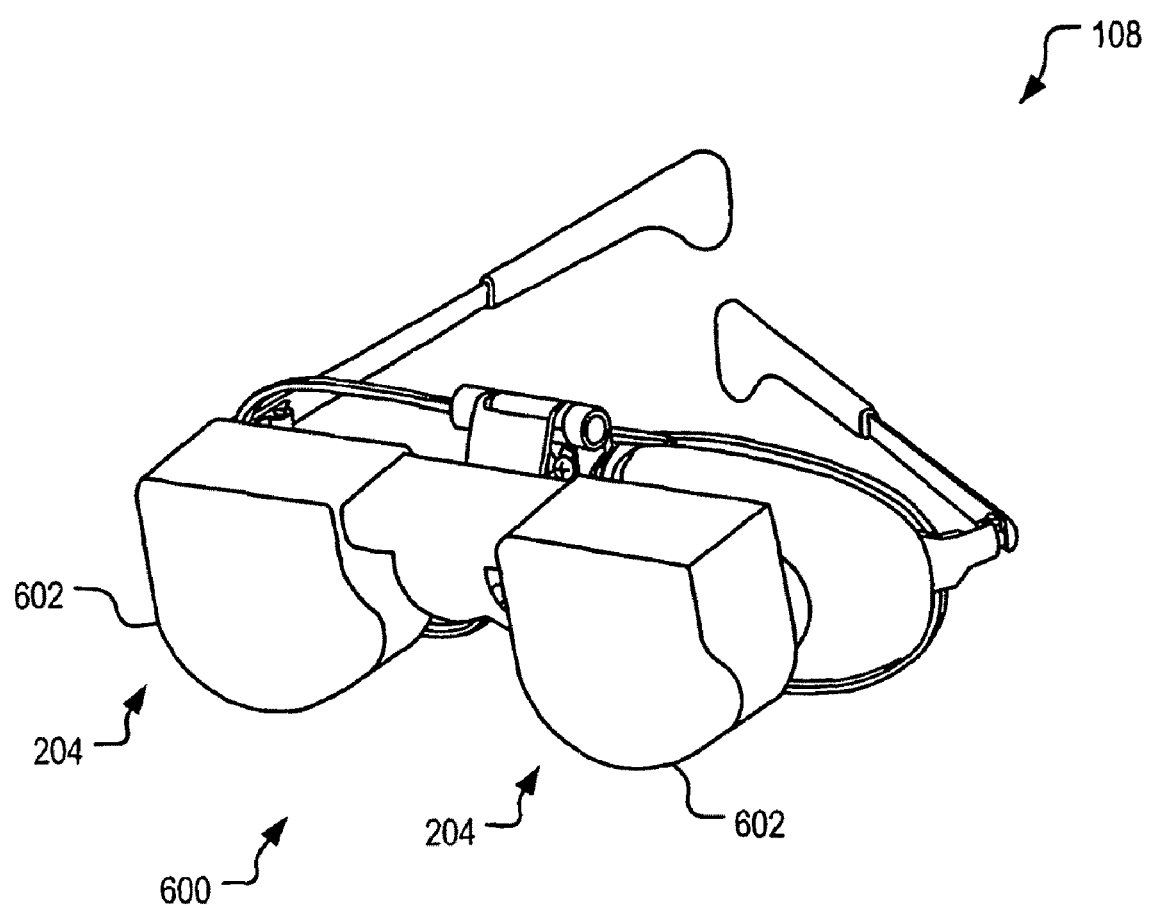
FIG. 6 is a perspective view of a third embodiment a lens simulator unit suitable for use with the system shown in FIG. 1.

Although the above-described examples of lens simulator units 102 include a head-mounted display that provides a display surface 204 for a single eye, in other embodiments a display surface 204 may be provided for each of the wearer's eyes. An embodiment, that provides a display surface 204 for each eye is expected to find application in binocular simulation. One example of a lens simulator unit including a head mounted display 600 having a pair of display surfaces is depicted in FIG. 6. In the depicted example, separate display surfaces 204 are contained within a respective housing 602, each of which also includes a separate display projector (not shown). Head-mounted projectors providing dual display surfaces 204 are presently commercially available, such as one available from Liteye Systems, Inc., Centennial, Colo., USA.

Figure 7:
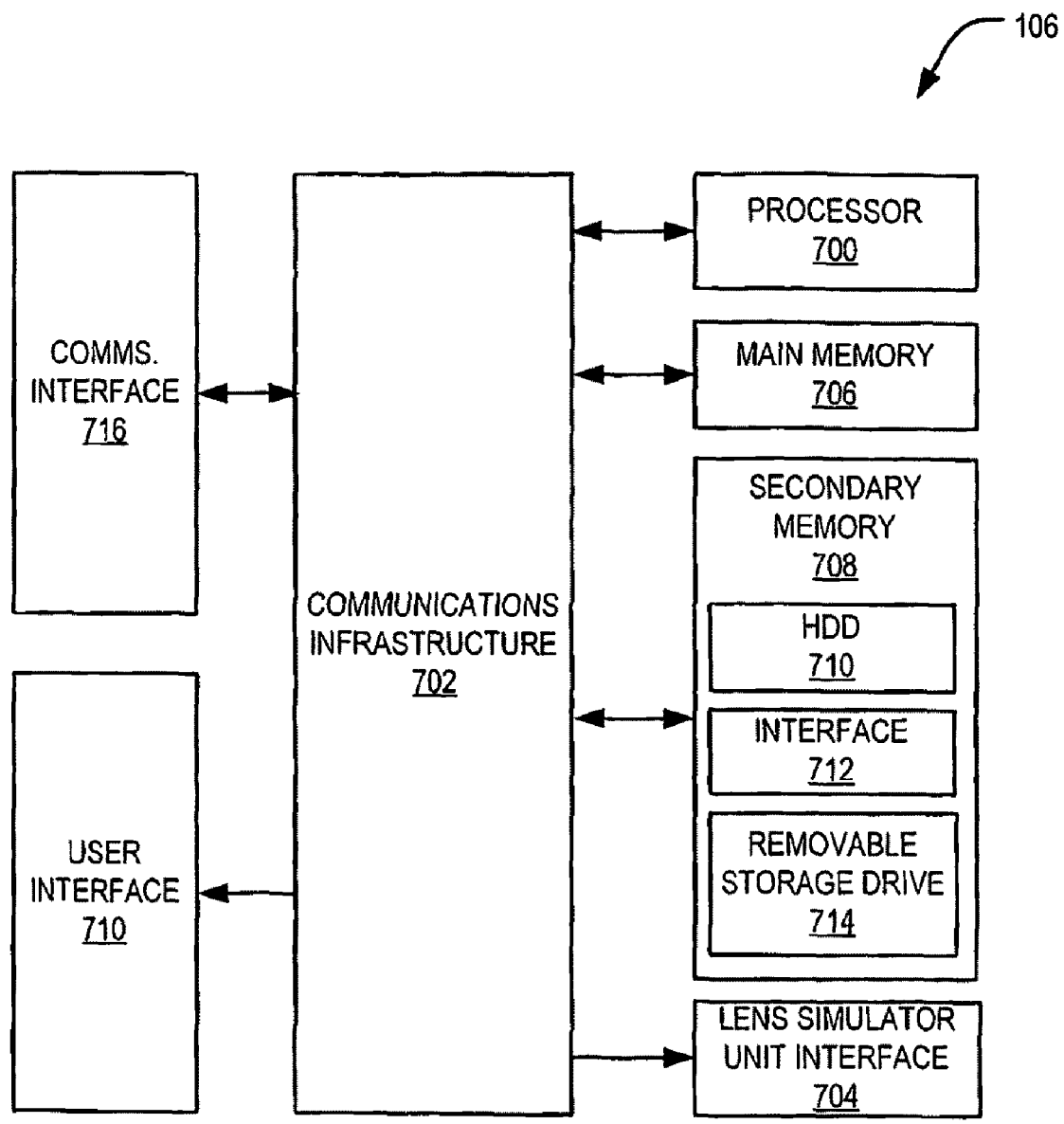
FIG. 7 is a block diagram of an embodiment of a computer system suitable for use with the system shown in FIG. 1.

Referring now to FIG. 7, the computer system 106 includes one or more processors, such as processor 700. The processor 700 is connected to a communication infrastructure 702, such as a bus.

The computer system 106 also includes a lens simulator unit interface 704 that may forward graphics, texts and other data from the communication infrastructure 702 for supply to the lens simulator unit 108 (ref. FIG. 1).

The computer system 106 also includes a main memory 706, preferably random access memory, and may also include a secondary memory 708.

The secondary memory 708 may include, for example, a hard disk drive, magnetic tape drive, optical disk drive, etc. The removable storage drive 714 reads from and/or writes to a removable storage unit (not shown) in a well known manner. The removable storage unit represents a floppy disk, magnetic tape, optical disk, etc.

As will be appreciated, the removable storage unit includes a computer usable storage medium having stored therein computer software in a form of a simulation engine comprising a series of instructions to cause the processor 700 to carry out desired functionality. In alternative embodiments, the secondary memory 708 may include other similar means for allowing computer programs or instructions to be loaded into the computer system 106. Such means may include, for example, a removable storage unit (such as an external USB storage device) and interface 712.

The computer system 106 may also include a communications interface 716. Communications interface 716 allows software and data to be transferred between the computer system 106 and external devices. Examples of communication interface 716 may include a modem, a network interface, a communications port, a PCMIA slot and card etc. Software and data transferred via a communications interface 716 are in the form of signals which may be electromagnetic, electronic, optical or other signals capable of being received by the communications interface 716. The signals are provided to communications interface 716 via a communications path (not shown) such as a wire or cable, fibre optics, phone line, cellular phone link, radio frequency or other communications channels.

The computer system 106 may also include one or more user interfaces, such as user interface 718. User interface 718 allows a user to interact with the computer system 106. Examples of user interface 716 may include a keyboard, a display (such as an LCD display), a mouse, a trackball, a touch surface etc.

Figure 8:
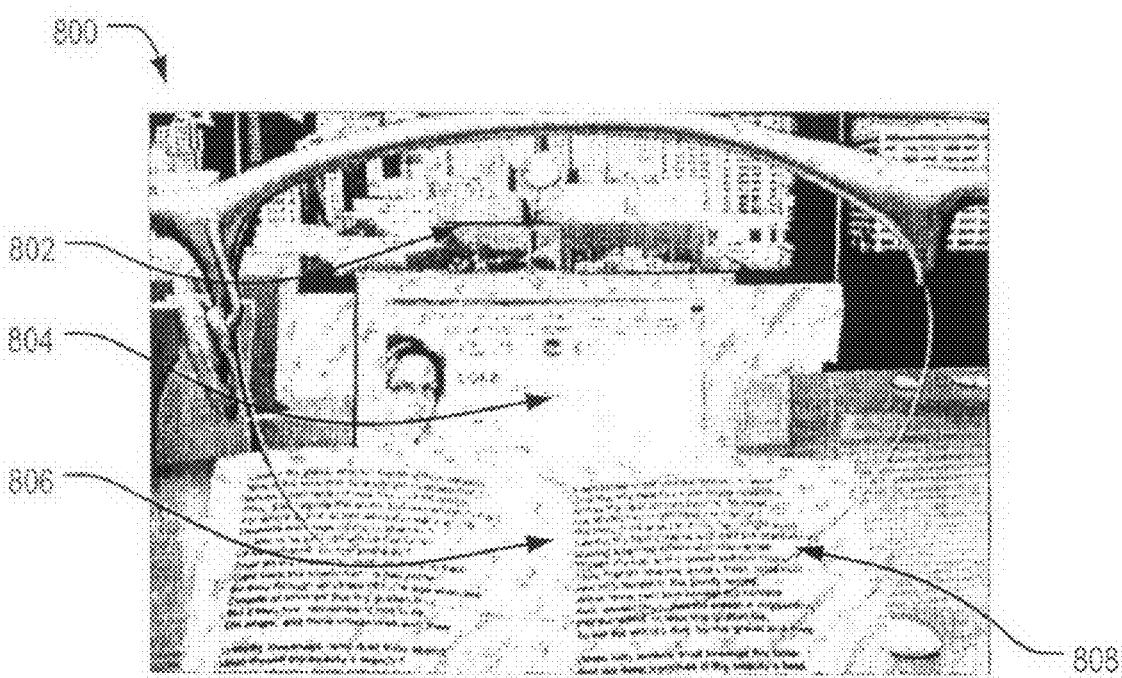
FIG. 8 is an example of an image for an image file.

Referring now to FIG. 8 there is shown an example of an initial output image 800 generated from an input image file prior to the processing step. In the depicted example, the initial output image 800 includes image features that are representative of objects 802 in a distance visual field (shown here as buildings), objects 802 in an intermediate visual field (shown here as a computer display), and objects 804 in a near visual field (shown here as a book). The initial input image 800 also includes a frame image feature 808 defining a reference boundary for a simulated field of view (FOV).

Figure 9:
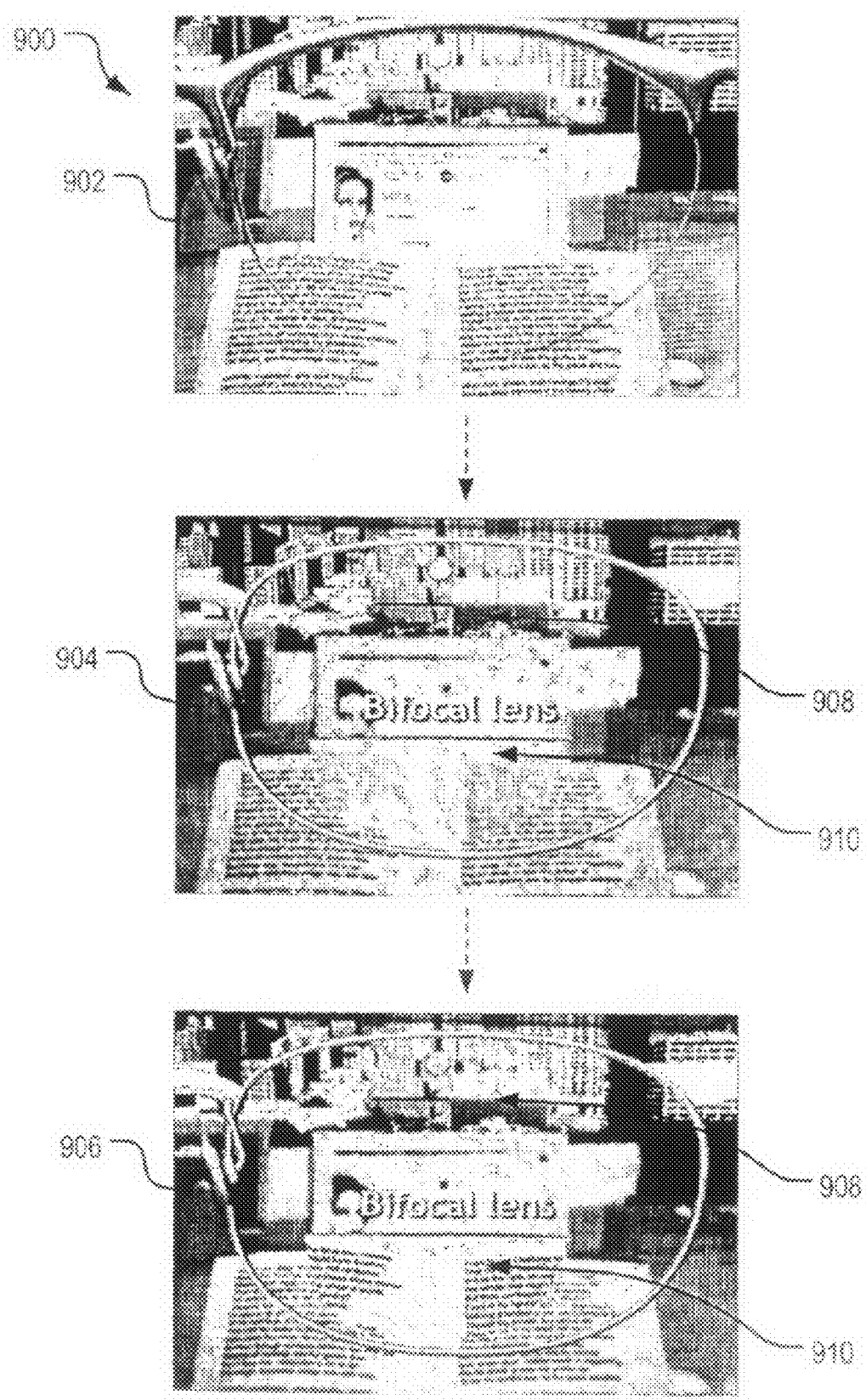
FIG. 9 is an example of a sequence of output images generated by a method in accordance with an embodiment.

Turning now to FIG. 9 there is shown a sequence 900 of images 902, 904, 906 depicting an example of the simulation of the optical effects of a bi-focal ophthalmic lens design. In this example, output image 902 corresponds with an input image. Image 904 is an output image that has been generated by processing simulation data and the input image 900 to simulate the optical effect of a bi-focal ophthalmic lens design on the wearer for viewing objects 908 in the distance field. As shown, the image features components representing near objects 910 have been "de-focussed" relative the initial output image 900 to simulate the optical effect of the wearer viewing through the distance segment of the bi-focal ophthalmic lens design to focus on the objects in the distance field.

Output image 906 is an output image that has been generated by processing simulation data and input image 900 to simulate the optical effect of a bi-focal ophthalmic lens design on the wearer for viewing objects in the near field. As shown, the image features representing near objects 910 have been "focussed" relative the input image 900 to simulate the optical effect of the wearer viewing through the near segment of the bi-focal ophthalmic lens design to focus on the objects 910 in the near field.

Figure 10:
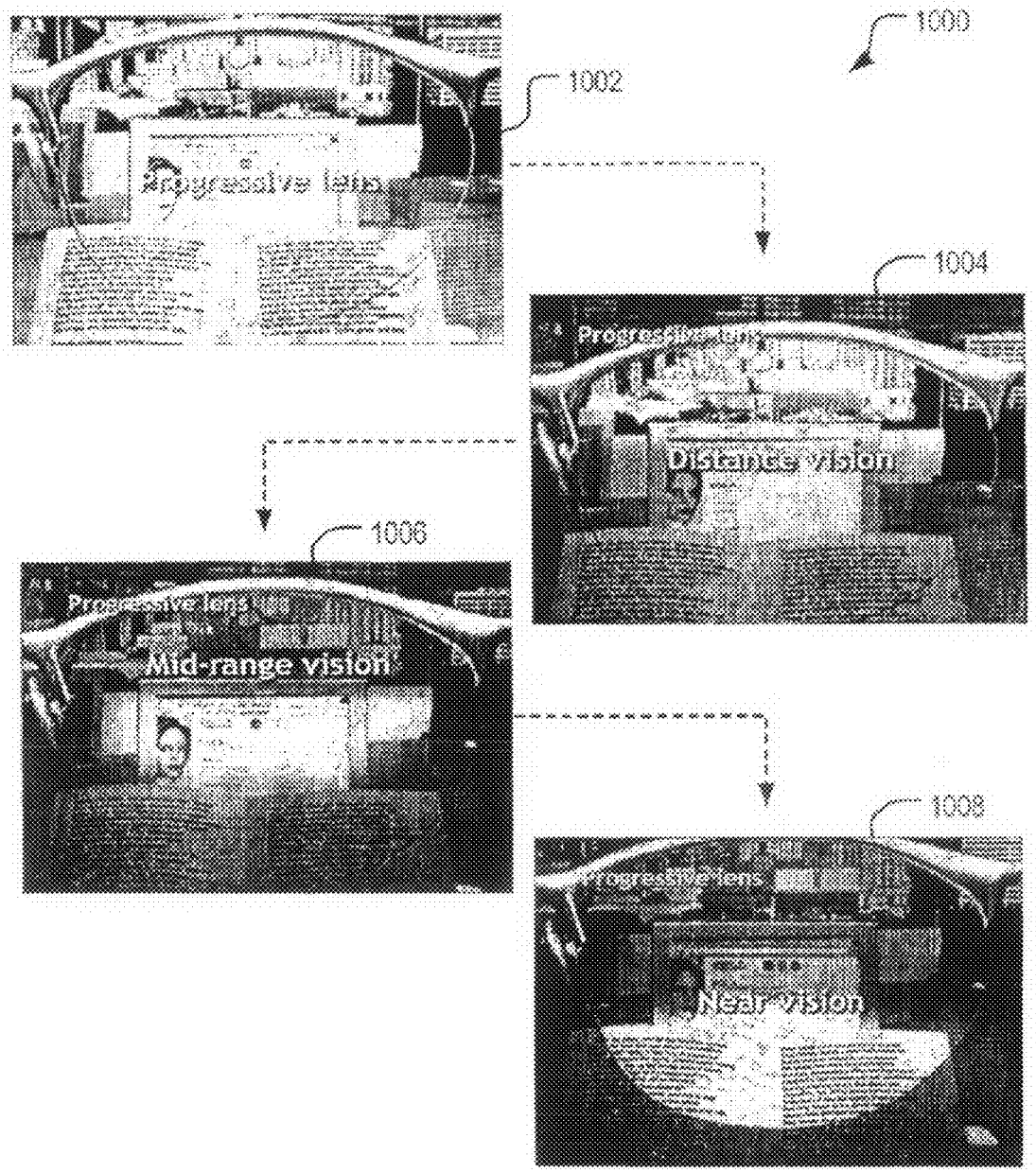
FIG. 10 is another example of a sequence of output images generated by a method in accordance with an embodiment.

Turning now to FIG. 10, there is shown a sequence 1000 of images 1002, 1004, 1006, 1008 simulating the optical effect of a progressive addition lens ophthalmic lens design on a wearer. The sequence is similar to that depicted in FIG. 9. However, in this example, the sequence simulates the optical effect of the simulated progressive addition lens for viewing objects in the distance (ref. image 1004), intermediate (ref. image 1006) and near field (ref. image 1008) using respective zones of the progressive addition lens.

Referring again to FIG. 1, it will thus be appreciated that a lens simulator 108 may simulate an optical effect of different types of ophthalmic lens designs, having different optical properties. In the present case, the computer system 106 stores simulation data for different single vision lens designs, different bi-focal lens designs and different progressive addition lens designs. Accordingly, in the present case the lens simulator 108 is capable of simulating a single vision lens, a bifocal lens or a progressive addition lens.

In addition to simulating an optical effect due to the optical properties of a selected ophthalmic lens design, the system 100 may also simulate an optical effect due to head movement of the wearer using a suitably configured lens simulator unit 108. In such an embodiment, the distortion matrix and or blur matrix is applied to the input image and updated each time the input image is update in accordance with head movement information.

Figure 11:
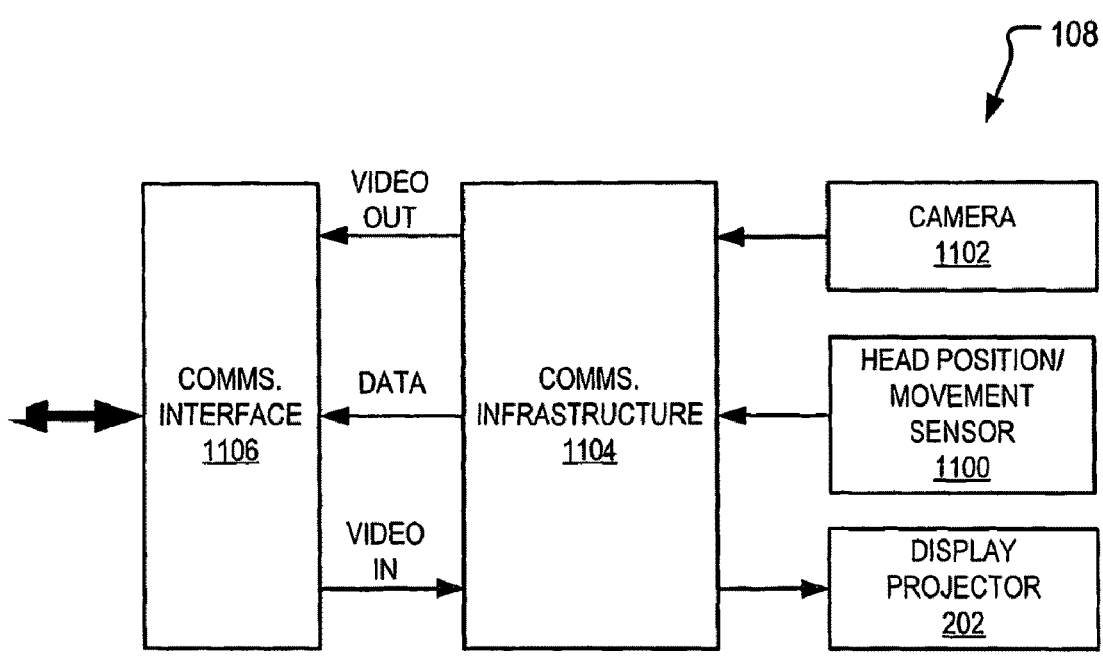
FIG. 11 is a block diagram for a lens simulator unit suitable for use with an embodiment of the present invention.

Referring to FIG. 11 there is shown one example of a lens simulator unit 108 for communicating head movement data obtained from a head movement/position sensor 1100 either before, or during a simulation that displays a computer generated "virtual" output image. In a system embodiment that uses head movement data, the computer system 106 (ref. FIG. 1) will provide suitable interfaces and software to receive the head movement data either, for example, during a viewing activity conducted prior to the simulation, or during viewing activity conducted the simulation itself. In such an embodiment, the simulation data will include the received head movement data so that the processing of the simulation data and the image file generates an output image file incorporating the motion induced effects, such as motion induced blur. The output image is preferably stabilised relative to head movements so as to maintain create a perception that the output image exists external to the lens simulator unit 108. Such an embedment also allows the lens model to interact with the scene in a similar manner to a real lens.

The lens simulator unit 108 shown in FIG. 11 also includes a camera, which may be used to capture a video image or a still image for a viewing activity conducted by the wearer prior to, or during, a simulation that generates an output image of a "real" scene, or that superimposes image features in the form of lens features over such a scene.

The camera 1102 is arranged to capture the "view" of the wearer during the viewing activity. The visual activity may include, for example, a near field viewing activity, such as reading, or a distance field viewing activity.

In an embodiment of the present invention that includes a lens simulator unit 108 of the type shown in FIG. 11, the processing of the input image file and the simulation data to generate an output image file may occur in advance of the display of the output image file. Accordingly, the input image file may be a pre-recorded input image file.

Alternatively, the simulation may involve processing the input image file and the simulation data to generate the output image for display in "real-time".

The lens simulator unit shown in FIG. 11 also includes communications infrastructure 1104, such as wires and cables for conveying video and data signals, and a communications interface 1106, such as connectors or drivers for connecting the lens simulator unit to the computer system 106.

Although in the above described embodiments the invention is implemented primarily using computer software, in other embodiments the invention may be implemented primarily in hardware using, for example, hardware components such as an application specific integrated circuit (ASICs). Implementation of a hardware state machine so as to perform the functions described herein will be apparent to persons skilled in the relevant art. In other embodiments, the invention may be implemented using a combination of both hardware and software.

Finally, it will be understood that there may be other variations and modifications to the configurations described herein that are also within the scope of the present invention.

The invention claimed is:

1. A method of simulating an optical effect and/or characteristic of a selected ophthalmic lens design for a wearer, the method including:
    retrieving simulation information for the selected ophthalmic lens design;
    processing the simulation information to generate output image data for an output image simulating the optical effect and/or characteristic of the selected ophthalmic lens design;
    displaying, using a head-mounted lens simulator unit worn by the wearer, the output image for viewing by the wearer; and
    wherein the simulated optical effect and/or characteristic includes the approximate visual experience that would be experienced by the wearer when viewing through an ophthalmic lens corresponding to the selected ophthalmic lens design.

2. A method according to claim 1 wherein the optical effect includes a simulated optical effect due one or more simulated optical parameters of the selected ophthalmic lens design, the one or more simulated parameters including:
    (a) sphere (Rx);
    (b) cylinder (Cyl);
    (c) axis;
    (d) addition power;
    (e) astigmatism;
    (f) prism; and
    (g) base.

3. A method according to claim 1 wherein the simulation information includes one or more of:
    (a) lens model information for the selected ophthalmic lens design; or
    (b) input image information.

4. A method according to claim 3 wherein the lens model information includes one or more of:
    (a) information in the form of a blur matrix; and
    (b) information in the form of a distortion matrix.

5. A method according to claim 3 wherein the input image information includes one of:
    (a) an image obtained from a camera; and
    (b) a computer generated image.

6. A method according to claim 1 wherein simulated characteristic include lens features, and wherein the output image includes the lens features superimposed over an input image.

7. A method according to claim 6 wherein the simulated lens features include lens boundaries.

8. A method according to claim 6 wherein the selected lens is a progressive addition ophthalmic lens and wherein the lens features include one or more of:
    (a) distance zone features;
    (b) corridor features; and
    (c) near zone features.

9. A method according to claim 6 wherein the selected lens is a bi-focal lens and wherein the features include the bi-focal segments.

10. A method of simulating an optical effect and/or characteristic of a selected ophthalmic lens design for a wearer, the method including:
    providing an input image capturing a viewing activity undertaken by the wearer;
    retrieving simulation information for the selected ophthalmic lens design;
    processing the input image and the simulation information to generate, for display to the wearer, an output image simulating the optical effect and/or characteristic of the selected ophthalmic lens design;
    displaying, using a head-mounted display worn by the wearer, the output image for viewing by the wearer; and
    wherein the simulated optical effect and/or characteristic includes the approximate visual experience that would be experienced by the wearer when viewing through an ophthalmic lens corresponding to the selected ophthalmic lens design.

11. A system for simulating the optical effect and/or characteristic of an ophthalmic lens design for a wearer, the system including:
    a simulation file containing simulation information for the selected ophthalmic lens design;
    a programmed computer including a simulation engine for processing the simulation information to generate output image data for an output image simulating the optical effect and/or characteristic of the selected ophthalmic lens design;
    a lens simulator including a head-mountable display for displaying the output image to the wearer; and
    wherein the simulated optical effect and/or characteristic includes the approximate visual experience that would be experienced by the wearer when viewing through an ophthalmic lens corresponding to the selected ophthalmic lens design.

12. A system for simulating an optical effect and/or characteristic of a selected ophthalmic lens design for a wearer, the system including processor and associated memory device for storing a series of instructions to cause the processor to:
retrieve simulation information for the selected ophthalmic lens design;
process the simulation information to generate output image data for an output image simulating the optical effect and/or characteristic of the selected ophthalmic lens design;
displaying, using a head-mounted lens simulator unit worn by the wearer, the output image for viewing by the wearer; and
wherein the simulated optical effect and/or characteristic includes the approximate visual experience that would be experienced by the wearer when viewing through an ophthalmic lens corresponding to the selected ophthalmic lens design.

13. Computer software for use in a system for simulating an optical effect and/or characteristic of a selected ophthalmic lens design for a wearer, the system including a processor and associated memory device for storing the computer software including a series of instructions to cause the processor to:
retrieve simulation information for the selected ophthalmic lens design;
process the simulation information to generate output image data for an output image simulating the optical effect and/or characteristic of the selected ophthalmic lens design;
displaying, using a head-mounted lens simulator unit worn by the wearer, the output image for viewing by the wearer; and
wherein the simulated optical effect and/or characteristic includes the approximate visual experience that would be experienced by the wearer when viewing through an ophthalmic lens corresponding to the selected ophthalmic lens design.

* * * * *